(12) United States Patent
Takada et al.

(10) Patent No.: US 10,182,889 B2
(45) Date of Patent: Jan. 22, 2019

(54) MAGNET ASSEMBLY FOR DENTAL MAGNETIC ATTACHMENT

(71) Applicant: HITACHI METALS, LTD., Tokyo (JP)

(72) Inventors: Yukyo Takada, Sendai (JP); Masatoshi Takahashi, Sendai (JP); Akira Kikuchi, Takasaki (JP)

(73) Assignee: HITACHI METALS, LTD., Tokyo (JP)

(*) Notice: Subject to any disclaimer, the term of this patent is extended or adjusted under 35 U.S.C. 154(b) by 0 days.

(21) Appl. No.: 15/300,003

(22) PCT Filed: Mar. 19, 2015

(86) PCT No.: PCT/JP2015/058360
§ 371 (c)(1),
(2) Date: Sep. 28, 2016

(87) PCT Pub. No.: WO2015/151845
PCT Pub. Date: Oct. 8, 2015

(65) Prior Publication Data
US 2017/0143455 A1     May 25, 2017

(30) Foreign Application Priority Data

Apr. 4, 2014   (JP) ................. 2014-077451

(51) Int. Cl.
*A61C 13/235*   (2006.01)
*A61C 8/00*   (2006.01)
(Continued)

(52) U.S. Cl.
CPC .............. *A61C 8/0081* (2013.01); *A61C 8/00* (2013.01); *A61C 13/235* (2013.01); *B23K 31/02* (2013.01);
(Continued)

(58) Field of Classification Search
CPC ........ A61C 8/0081; A61C 8/00; B23K 31/02; B23K 2203/05; B23K 2203/04;
(Continued)

(56) References Cited

U.S. PATENT DOCUMENTS

| 5,788,493 | A | * | 8/1998 | Tanaka | ................. | A61C 8/0081 |
| | | | | | | 433/189 |
| 2004/0241612 | A1 | * | 12/2004 | Yamaguchi | .......... | A61C 13/235 |
| | | | | | | 433/189 |

(Continued)

FOREIGN PATENT DOCUMENTS

| CN | 101384742 A | 3/2009 |
| CN | 201879855 U | 6/2011 |

(Continued)

OTHER PUBLICATIONS

International Search Report for PCT/JP2015/058360 dated Jun. 16, 2015 [PCT/ISA/210].

(Continued)

*Primary Examiner* — Yogesh Patel
*Assistant Examiner* — Gwen M Demosky
(74) *Attorney, Agent, or Firm* — Sughrue Mion, PLLC (57) ABSTRACT

A magnet assembly for a dental magnetic attachment comprising a cup-shaped yoke of substantially Ni-free ferritic stainless steel, a permanent magnet received in a recess of the cup-shaped yoke, a seal member sealing an opening of the cup-shaped yoke, and an abutment-welded portion of the seal member and the cup-shaped yoke; the seal member comprising a center portion of substantially Ni-free ferritic stainless steel; an intermediate portion of substantially Ni-free austenitic stainless steel having a nitrogen content of 0.5-2.0% by mass, and a peripheral portion made of sub- (Continued)

stantially Ni-free ferritic stainless steel having a nitrogen content of 1.3% or less by mass, smaller than in the intermediate portion.

14 Claims, 7 Drawing Sheets (51) Int. Cl.
| | |
|---|---|
| C23C 8/26 | (2006.01) |
| C23C 8/80 | (2006.01) |
| C22C 38/00 | (2006.01) |
| C22C 38/40 | (2006.01) |
| C21D 6/00 | (2006.01) |
| C21D 8/12 | (2006.01) |
| C23C 8/02 | (2006.01) |
| B23K 31/02 | (2006.01) |
| C21D 9/52 | (2006.01) |
| C22C 38/44 | (2006.01) |
| B23K 103/04 | (2006.01) |

(52) U.S. Cl.
CPC ............ *C21D 6/002* (2013.01); *C21D 6/004* (2013.01); *C21D 8/12* (2013.01); *C21D 9/525* (2013.01); *C22C 38/00* (2013.01); *C22C 38/001* (2013.01); *C22C 38/40* (2013.01); *C22C 38/44* (2013.01); *C23C 8/02* (2013.01); *C23C 8/26* (2013.01); *C23C 8/80* (2013.01); B23K 2103/05 (2018.08); C21D 2211/005 (2013.01); C21D 2251/04 (2013.01)

(58) Field of Classification Search
CPC ........ C21D 6/004; C21D 6/002; C21D 9/525; C21D 2211/005; C21D 2251/04; C22C 38/001; C22C 38/44; C23C 8/24
USPC .......................................... 433/189, 167–172
See application file for complete search history.

(56) References Cited

U.S. PATENT DOCUMENTS

| 2007/0186999 | A1* | 8/2007 | Kuroda | ................... C23C 8/26 148/217 |
| 2008/0251163 | A1* | 10/2008 | Chiba | .................. A61K 6/0044 148/512 |
| 2009/0065098 | A1 | 3/2009 | Soshiroda et al. | |
| 2013/0304184 | A1* | 11/2013 | Taguchi | ................ C22C 38/001 623/1.11 |
| 2014/0141387 | A1* | 5/2014 | Kikuchi | ............... A61C 13/235 433/174 |
| 2015/0173871 | A1 | 6/2015 | Kyotani et al. | |
| 2015/0332820 | A1* | 11/2015 | Ishikawa | ................ C21D 10/00 335/296 |

FOREIGN PATENT DOCUMENTS

| JP | 5-95965 A | 4/1993 | |
| JP | H0595965 * | 4/1993 | ............... A61C 8/00 |
| JP | 11-137576 A | 5/1999 | |
| JP | 2007-51368 A | 3/2007 | |
| JP | 4288505 B2 * | 7/2009 | .......... A61C 8/0081 |
| JP | 2012-92413 A | 5/2012 | |
| JP | 2014-33872 A | 2/2014 | |
| JP | 2014-73302 A | 4/2014 | |

OTHER PUBLICATIONS

Communication dated Nov. 24, 2017 from the European Patent Office in counterpart European application No. 15773558.0.
Chinese Office Action for Application No. 201580017157.8 dated May 22, 2018 by the State Intellectual Property Office of the People's Republic of China, 11 pages including translations.
Cast Iron Valve, edited by Cast Iron Valve Editorial Board, China Machine Press, Sep. 1993, 9 pages.

* cited by examiner

MAGNET ASSEMBLY FOR DENTAL MAGNETIC ATTACHMENT

CROSS REFERENCE TO RELATED APPLICATIONS

This application is a National Stage of International Application No. PCT/JP2015/058360, filed on Mar. 19, 2015 (which claims priority from Japanese Patent Application No. 2014-077451, filed on Apr. 4, 2014), the contents of which are incorporated herein by reference in their entirety.

FIELD OF THE INVENTION

The present invention relates to a magnet assembly for a dental magnetic attachment for holding a denture utilizing the magnetic attraction of a permanent magnet.

BACKGROUND OF THE INVENTION

Figure 9:
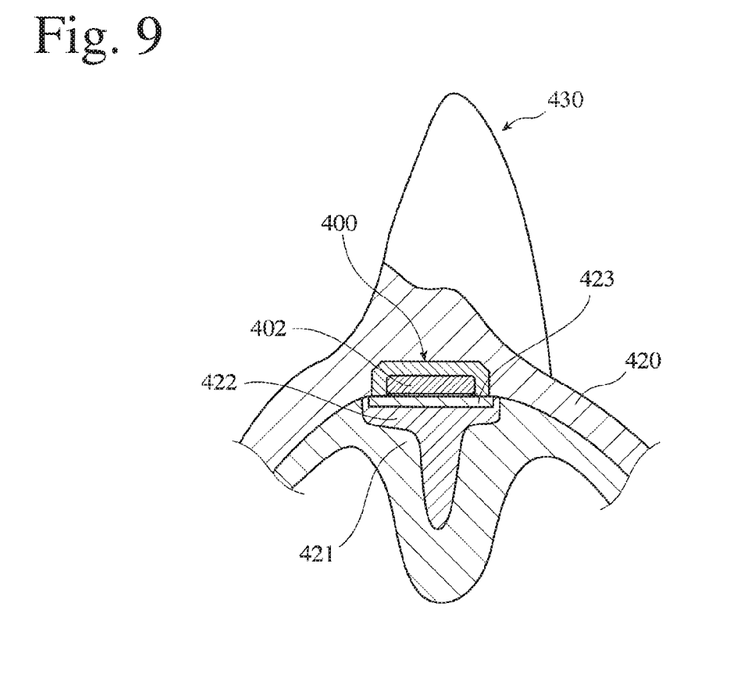
FIG. 9 is a schematic cross-sectional view showing a denture comprising a magnet assembly for a magnetic attachment, which is attached to a keeper fixed to a root cap implanted in an alveolus.
Figure 10:
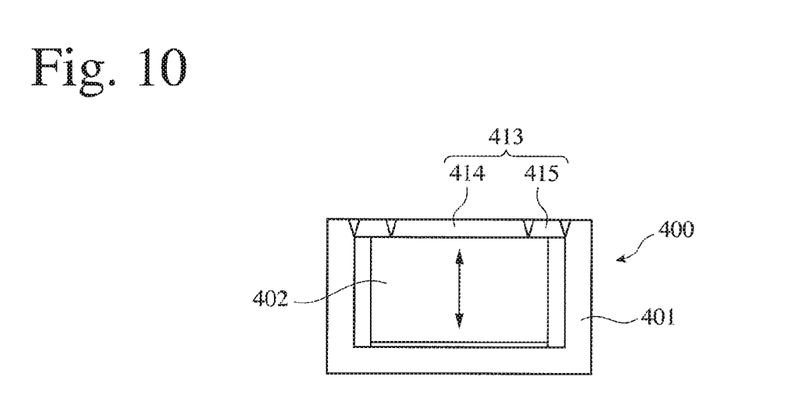
FIG. 10 is a schematic cross-sectional view showing a conventional magnet assembly for a magnetic attachment.

As shown in FIG. 10, a magnet assembly 400 for a dental magnetic attachment has a structure comprising a soft-magnetic stainless steel disc yoke 414 and a non-magnetic stainless steel seal ring 415 concentrically arranged in an opening of a soft-magnetic stainless steel cup-shaped yoke 401; welding being made between the disc yoke 414 and the seal ring 415 and between the seal ring 415 and the cup-shaped yoke 401 along their entire boundaries to seal a permanent magnet 402. As shown in FIG. 9, this magnet assembly 400 is embedded in a denture floor 420 of denture 430, and held by a root cap 422 embedded in an alveolus 421 by magnetic attraction between the magnet assembly 400 and a soft-magnetic keeper 423 attached to the root cap 422. The magnet assembly 400 should meet requirements such as no harm to a human body, a long period of chemical stability, large attraction, etc.

For example, as described in JP 5-95965 A, the magnet assembly 400 for a dental magnetic attachment is produced by placing a permanent magnet 402 (for example, a neodymium magnet) in a recess of the cup-shaped yoke 401, inserting a disc-shaped seal member 413 composed of the disc yoke 414 and the seal ring 415 into an opening of the cup-shaped yoke 401, welding an abutment of the cup-shaped yoke 401 and the seal ring 415, and an abutment of the seal ring 415 and the disc yoke 414 for sealing, and then making the welded portions flat by polishing or grinding. When this magnet assembly 400 is attracted to the keeper 423, the seal ring 415 of austenitic stainless steel existing in a peripheral portion of the disc-shaped seal member 413 shuts part of a magnetic path, so that a magnetic flux of the permanent magnet 402 can efficiently flow through a magnetic circuit constituted by the keeper 423, the cup-shaped yoke 401 and the disc yoke 414, resulting in large attraction.

The disc-shaped seal member 413 is generally produced by inserting a round rod of ferritic stainless steel into an austenitic stainless steel pipe, conducting drawing to form a round clad rod comprising a peripheral portion of austenitic stainless steel and a center portion of ferritic stainless steel, and transversely cutting it. Conventionally used for the seal ring 415 is austenitic stainless steel obtained by forming an austenite phase by dissolving nickel. However, a nickel-containing magnet assembly for a magnetic attachment cannot be used for patients having nickel allergy. Thus desired for a dental magnetic attachment is a magnet assembly of nickel-free stainless steel.

As nickel-free austenitic stainless steel, for example, JP 2012-92413 A discloses nitrogen-dissolved austenitic stainless steel obtained by dissolving nitrogen in a stainless steel composition, and proposes a method for producing nitrogen-dissolved austenitic stainless steel by heating ferritic stainless steel at 1100-1250° C. in a nitrogen atmosphere at about atmospheric pressure (partial pressure of nitrogen: 80-86.7 kPa), so that the ferritic stainless steel surface absorbs nitrogen.

However, because the nitrogen-dissolved austenitic stainless steel is transformed to have a mixed phase of ferrite and Cr nitride at a high temperature of about 700° C. or higher and at atmospheric pressure, this material cannot be heated for abutment welding or extrusion to form a pipe for the seal ring, or the annealing of a pipe to remove strain.

OBJECT OF THE INVENTION

Accordingly, an object of the present invention is to provide a low-cost, nickel-free, magnet assembly for a dental magnetic attachment, which exhibits attraction and durability not lower than conventional levels.

DISCLOSURE OF THE INVENTION

As a result of intensive research in view of the above object, the inventors have found that by dissolving nitrogen to a predetermined thickness in a peripheral portion of a round rod of substantially Ni-free ferritic stainless steel, denitriding only a surface layer portion of the nitrogen-dissolved portion to provide a round rod integrally having a core portion of ferritic stainless steel, an intermediate portion of austenitic stainless steel, and a surface layer portion of ferritic stainless steel, and then cutting the round rod to a disc, a disc-shaped seal member comprising a center portion of substantially Ni-free ferritic stainless steel, an intermediate portion of substantially Ni-free austenitic stainless steel, and a peripheral portion of substantially Ni-free ferritic stainless steel is obtained; and that when the disc-shaped seal member is welded to a cup-shaped yoke receiving a permanent magnet, a nitrogen gas is less generated (less denitriding occurs) by welding heat, because the peripheral portion is made of nitrogen-free ferritic stainless steel, resulting in a substantially nickel-free magnet assembly for a dental magnetic attachment having excellent magnetic attraction with little welding defect. The present invention has been completed based on such findings.

Thus, the magnet assembly of the present invention for a dental magnetic attachment comprises a cup-shaped yoke of substantially Ni-free ferritic stainless steel, a permanent magnet received in a recess of the cup-shaped yoke, a seal member sealing an opening of the cup-shaped yoke, and an abutment-welded portion of the seal member and the cup-shaped yoke; the seal member comprising a center portion of substantially Ni-free ferritic stainless steel;

an intermediate portion outside the center portion, which is made of substantially Ni-free austenitic stainless steel having a nitrogen content of 0.5-2.0% by mass; and a peripheral portion outside the intermediate portion, which is made of substantially Ni-free ferritic stainless steel having a nitrogen content of 1.3% or less by mass, smaller than in the intermediate portion.

A center of the welded portion is preferably deviated from an abutment boundary of the seal member and the cup-shaped yoke toward the cup-shaped yoke.

The cup-shaped yoke and the seal member preferably have a Ni content of 0.2% or less by mass.

The cup-shaped yoke and the seal member preferably have a Cr content of 17-32% by mass.

The average radial length of the peripheral portion is preferably 20-80% of the radial length of the welded portion.

The average radial length of the peripheral portion is preferably 50-400 μm.

The average radial length of the intermediate portion is preferably 50-400 μm.

The average radial length of the intermediate portion is preferably larger than the average radial length of the peripheral portion.

In a boundary of the intermediate portion of austenitic stainless steel and the center portion of ferritic stainless steel, part of the austenitic stainless steel of the intermediate portion is preferably transformed to a ferrite phase or a mixed phase of ferrite and Cr nitride by heating.

EFFECTS OF THE INVENTION

Because the magnet assembly of the present invention for a dental magnetic attachment has high attraction and durability without containing nickel, it can be used for patients having an allergy to nickel. Because the magnet assembly of the present invention for a dental magnetic attachment can be produced more easily than conventional ones, its production cost is low.

DESCRIPTION OF THE PREFERRED EMBODIMENTS (1) Overall Structure

Figure 1A:
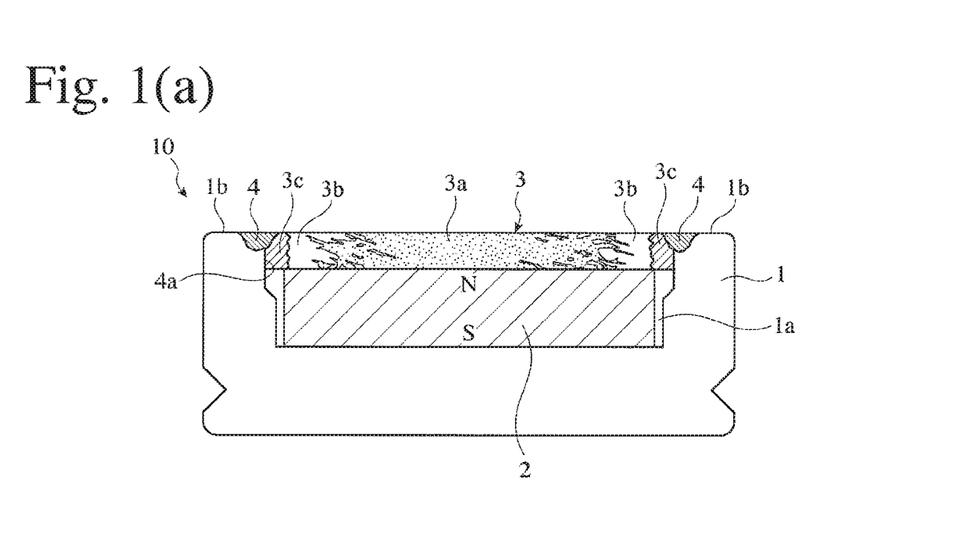
FIG. 1(a) is a schematic cross-sectional view showing an example of the magnet assemblies of the present invention for a magnetic attachment.
Figure 1B:
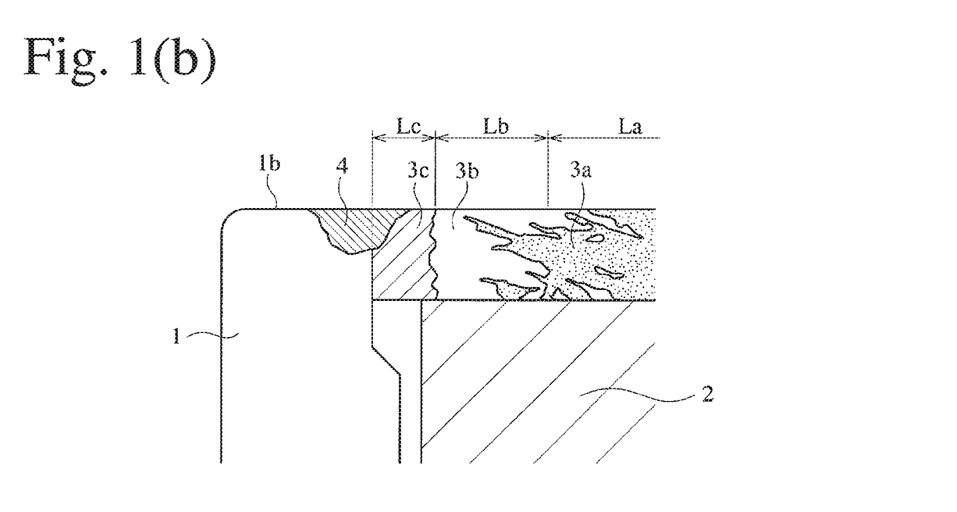
FIG. 1(b) is a schematic cross-sectional view enlargedly showing a welded portion in the magnet assembly for a magnetic attachment shown in FIG. 1(a).

As shown in FIGS. 1(a) and 1(b), the magnet assembly 10 for a magnetic attachment comprises a cup-shaped yoke 1 of substantially Ni-free ferritic stainless steel, which has an opening on one side, a permanent magnet 2 received in a recess 1a of the cup-shaped yoke 1, a seal member 3 sealing the opening of the cup-shaped yoke 1, and a welded portion 4 of the abutment portion 4a of the seal member 3 and the cup-shaped yoke 1; the seal member 3 comprising a center portion 3a of substantially Ni-free ferritic stainless steel; an intermediate portion 3b outside the center portion 3a, which is made of substantially Ni-free austenitic stainless steel having a nitrogen content of 0.5-2.0% by mass; and a peripheral portion 3c outside the intermediate portion 3b, which is made of substantially Ni-free ferritic stainless steel having a nitrogen content of 1.3% or less by mass, smaller than in the intermediate portion 3b. The Cr content of the cup-shaped yoke 1 and the seal member 3 is preferably 17-32% by mass, more preferably 24-32% by mass. The Ni content of the cup-shaped yoke 1 and the seal member 3 is preferably 0.2% or less by mass, more preferably 0.1% or less by mass. A center of the welded portion 4 may be deviated from the abutment boundary 4a of the seal member 3 and the cup-shaped yoke 1 toward the cup-shaped yoke 1.

In this magnet assembly 10 for a magnetic attachment, the ferritic stainless steel cup-shaped yoke 1, the ferritic stainless steel center portion 3a, and the ferritic stainless steel peripheral portion 3c are magnetic, while the austenitic stainless steel intermediate portion 3b is non-magnetic, constituting a magnetic circuit having one pole (N pole in the figure) in the center portion 3a of the seal member 3, and the other pole (S pole in the figure) in an opening-side end portion 1b of the cup-shaped yoke 1.

(2) Seal Member

Figure 2:
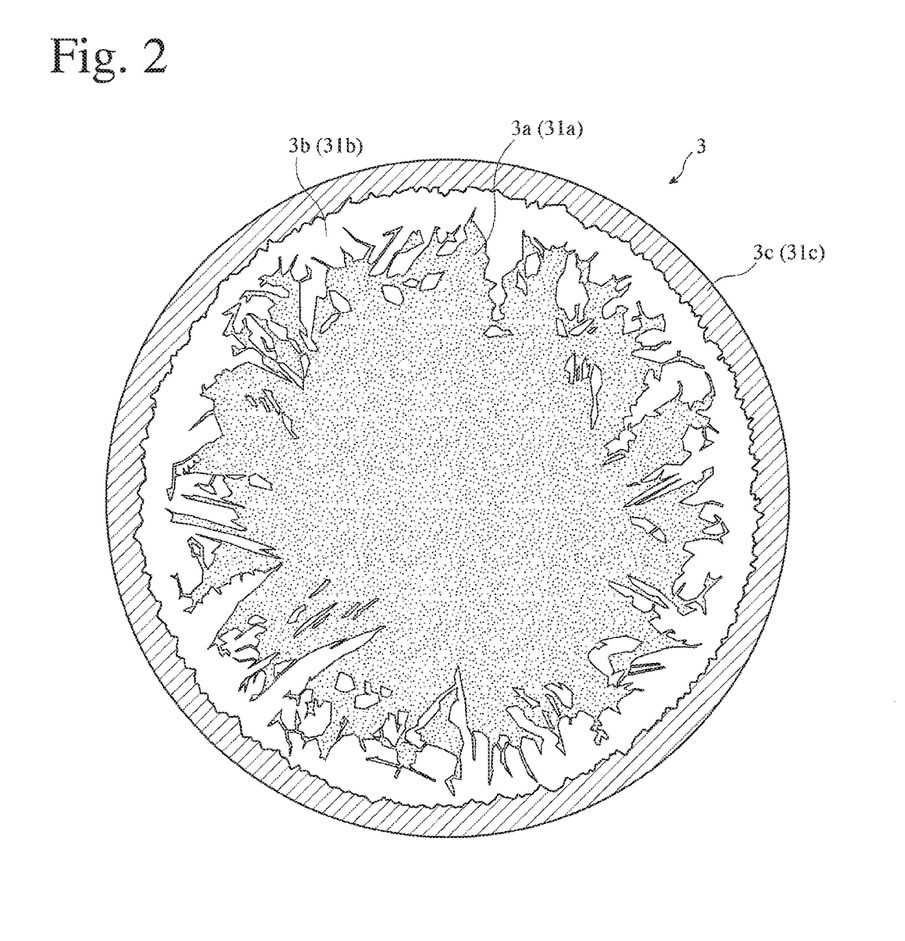
FIG. 2 is a schematic view showing an example of seal members.

As shown in FIG. 2, the seal member 3, which is a member sealing the permanent magnet 2 in the recess 1a of the cup-shaped yoke 1 and constituting a magnetic circuit, comprises a center portion 3a of ferritic stainless steel; an intermediate portion 3b outside the center portion 3a, which is made of austenitic stainless steel having a nitrogen content of 0.5-2.0% by mass; and a peripheral portion 3c outside the intermediate portion 3b, which is made of ferritic stainless steel having a nitrogen content of 1.3% or less by mass, smaller than in the intermediate portion 3b. The austenitic stainless steel of the intermediate portion 3b is formed by dissolving nitrogen in ferritic stainless steel, its nitrogen content varying depending on the Cr content of the stainless steel.

The seal member 3 is made of substantially Ni-free stainless steel, preferably corrosion-resistant, soft-magnetic ferritic stainless steel (SUS447J1, SUSXM27, SUS444, etc.). The Cr content of the stainless steel is preferably 17-32% by mass, more preferably 24-32% by mass. The cup-shaped yoke 1 and the seal member 3 are not restricted to be circular, but may be elliptical or polygonal such as square, etc. In this case, the shape of the permanent magnet 2 may be changed according to those of the cup-shaped yoke 1 and the seal member 3, if necessary.

When the seal member 3 has a circular shape, its diameter is determined depending on the magnet assembly for a dental magnetic attachment, usually 1800-5500 μm. The average radius La of the center portion 3a is preferably 800-5000 μm, more preferably 1000-4000 μm. The average radial length Lb of the intermediate portion 3b is preferably 50-400 μm, more preferably 100-300 μm. The average radial length Lc of the peripheral portion 3c is preferably 50-400 μm, more preferably 75-300 μm. The average radial length Lb of the intermediate portion 3b is preferably larger than the average radial length Lc of the peripheral portion 3c.

The intermediate portion 3b of the seal member 3 is made of substantially Ni-free austenitic stainless steel having a nitrogen content of 0.5-2.0% by mass. When the nitrogen content is less than 0.5% by mass, unstable austenitic stainless steel is likely ferritized. When the nitrogen content is more than 2.0% by mass, nitride is likely precipitated. The nitrogen content is more preferably 0.7-1.8% by mass.

The peripheral portion 3c of the seal member 3 is made of substantially Ni-free ferritic stainless steel having a nitrogen content of 1.3% or less by mass, smaller than in the intermediate portion 3b. The nitrogen content is preferably 1.0% or less by mass, more preferably 0.5% or less by mass. A smaller nitrogen content is preferable, though a trace amount of nitrogen is permitted. The peripheral portion 3c is obtained by ferritization by denitriding austenitic stainless steel having a nitrogen content of 0.5% or more by mass, effective in reducing the amount of a nitrogen gas generated when the cup-shaped yoke 1 and the seal member 3 are welded, as described later. Accordingly, the peripheral portion 3c preferably has such a width (radial length) that the welded portion 4 does not reach the intermediate portion 3b, namely, such a width as to avoid the intermediate portion 3b from being denitrided by heating by laser irradiation during welding.

For example, when welding is conducted with a laser beam center located at the abutment boundary of the seal member 3 and the cup-shaped yoke 1, the average radial length Lc of the peripheral portion 3c is preferably at least half of the laser beam diameter. However, the laser beam center need not be at the abutment boundary, but may be deviated toward the cup-shaped yoke 1 or the seal member 3 from the aspect of weldability and a magnetic circuit. Accordingly, the average radial length Lc of the peripheral portion 3c is preferably 20-80% of the radial length of the welded portion 4.

The radial length of the welded portion 4 is measured in the radially widest portion of the welded portion 4, on the surface of the welded portion 4 as is clear from FIG. 1(b). Heat generated by laser irradiation is transmitted outward in the outermost portion of this welded portion 4, to melt stainless steel in a slightly wider range than the laser diameter. Because the melting range of stainless steel by laser irradiation varies depending on the diameter, power, scanning speed, etc. of laser beams, the radial length of the peripheral portion 3c is desirably determined, based not on the laser diameter, but on the radial length of the widest portion in the welded portion 4.

The seal member 3 is produced by subjecting a round rod of ferritic stainless steel to a nitrogen-dissolving treatment to austenize its surface layer portion to a predetermined depth, denitriding a surface portion of the austenized portion for ferritization, and then transversely cutting it to a disc shape, as described later. Accordingly, there are jagged boundaries between a ferritic stainless steel portion 31a of the center portion 3a and an austenitic stainless steel portion 31b of the intermediate portion 3b, and between an austenitic stainless steel portion 32b of the intermediate portion 3b and a ferritic stainless steel portion 31c of the peripheral portion 3c, as shown in FIG. 2. As is clear from FIG. 2, the boundary of the peripheral portion 3c and the intermediate portion 3b is less jagged than the boundary of the intermediate portion 3b and the center portion 3a.

Figure 3:
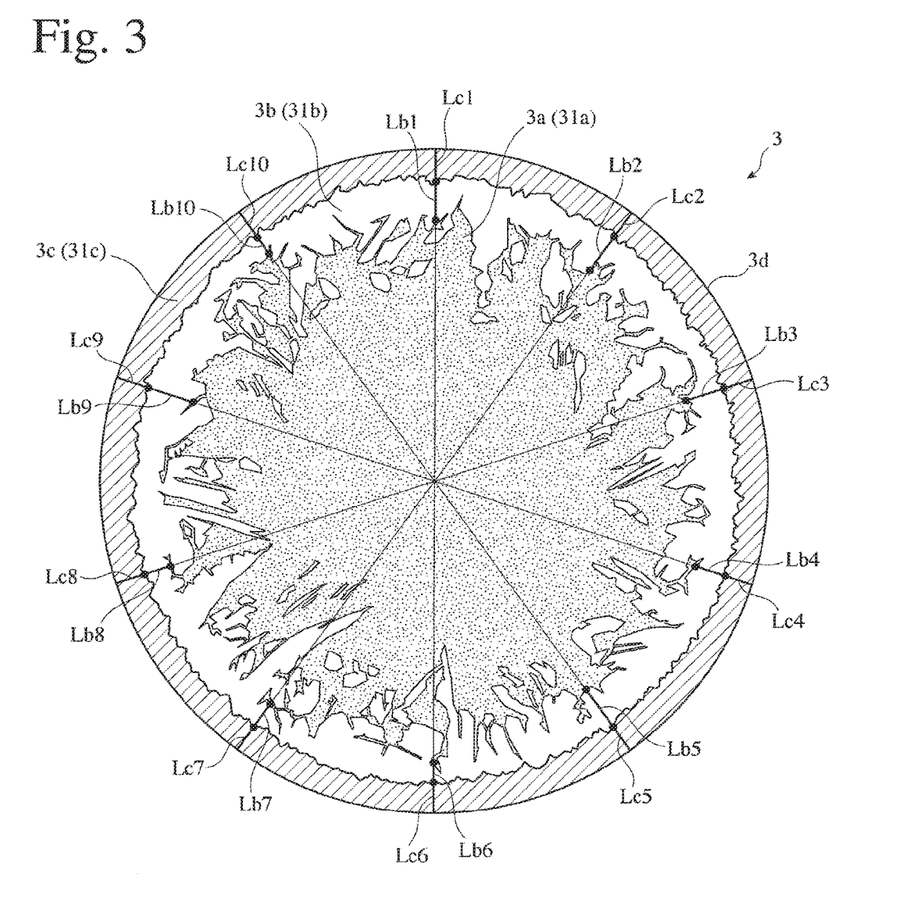
FIG. 3 is a schematic view showing methods for measuring the average radial lengths of a center portion, an intermediate portion and a peripheral portion in the seal member.

Accordingly, as shown in FIG. 3, the average radius La and average lengths Lb, Lc are determined by 10 radial lines drawn with the same circumferential angle intervals. The average length Lc of the ferritic stainless steel portion 31c of the peripheral portion 3c is determined by measuring each length Lc1-Lc10 from an outer peripheral end 3d to a crossing point of each line and the austenitic stainless steel portion 31b of the intermediate portion 3b, and averaging them. Similarly, the average length Lb of the austenitic stainless steel portion 31b of the intermediate portion 3b is determined by measuring each length Lb1-Lb10 from a crossing point of each line and the austenitic stainless steel portion 31b of the intermediate portion 3b to a crossing point of each line and the ferritic stainless steel portion 31a of the center portion 3a, and averaging them. The average radius La of the ferritic stainless steel portion 31a of the center portion 3a is determined by subtracting (Lc+Lb) from the radius of the seal member 3.

Nitrogen-Dissolving Treatment

The seal member 3 is produced by austenizing a round rod of corrosion-resistant, soft-magnetic ferritic stainless steel by a nitrogen-dissolving treatment, denitriding the round rod to ferritize only the outermost surface layer, and transversely slicing the treated round rod to a predetermined thickness. The nitrogen-dissolving treatment is conducted by heat-treating ferritic stainless steel at 1150-1250° C. in a nitrogen atmosphere (50 kPa or more), for example, in a vacuum heating apparatus. The vacuum heating apparatus is preferably filled with a nitrogen atmosphere at about atmospheric pressure, particularly at about 80-120 kPa. To prevent oxidation, the nitrogen gas used preferably does not contain oxygen and water. When the heating treatment temperature is lower than 1150° C., nitrogen is not dissolved sufficiently. When it is higher than 1250° C., the control of a nitrogen-dissolving speed is difficult, failing to obtain a nitrogen-dissolved austenitic stainless steel having a predetermined depth (radial width of the intermediate portion 3b of the seal member 3). The nitrogen-dissolved austenitic stainless steel should contain nitrogen in an amount of sufficiently austenizing the ferrite phase, and its nitrogen content is 0.5-2.0% by mass, though variable depending on the Cr content of stainless steel. The lower limit of the nitrogen content is preferably 1% by mass.

The nitrogen-dissolving treatment may be conducted by a method of heating ferritic stainless steel placed in a heating furnace, or a method of introducing ferritic stainless steel heated to a predetermined temperature into a heating furnace. In the method of heating stainless steel placed in the heating furnace, the temperature of the ferritic stainless steel is elevated preferably at a speed of about 5-20° C./min for uniform heating. A nitrogen gas may be charged into the furnace from the start of heating, or after a predetermined temperature is reached.

The heating treatment time (time of holding the highest temperature) is properly adjusted depending on the depth of austenization of ferritic stainless steel by a nitrogen-dissolving treatment. For example, austenization to the depth of about 300 μm can be achieved by a heating treatment at 1200° C. for about 2-4 hours in a nitrogen atmosphere at atmospheric pressure.

Denitriding

After the round rod of ferritic stainless steel is austenized to a predetermined depth from the surface by a nitrogen-dissolving treatment, the outermost surface layer of the austenized layer is denitrided for ferritization. Denitriding can be conducted by lowering nitrogen pressure in the nitriding treatment. The temperature is preferably kept constant. The nitrogen pressure in denitriding is preferably 99% or less, more preferably 95% or less, of the nitrogen pressure in nitriding. The nitrogen content of the denitrided ferrite phase is 1.3% or less by mass, preferably 1.0% or less by mass, more preferably 0.5% or less by mass.

To keep an austenite phase formed by the nitrogen-dissolving treatment and a ferrite phase formed by the denitriding treatment at room temperature, stainless steel is rapidly cooled from a high temperature after the nitrogen-dissolving treatment and the denitriding treatment. When the treated stainless steel is cooled slowly, the formed austenite phase is transformed to a ferrite phase or a mixed phase of ferrite and Cr nitride. The rapid cooling of stainless steel can be conducted by transferring the nitrogen-dissolved member into a cooling chamber in the heating apparatus, to cool it by a cooling gas such as a nitrogen gas, a rare gas, etc., or by water, etc.

The nitrogen-dissolved ferritic stainless steel round rod is desirably shorter than a constant-temperature section in a heating chamber of the furnace, because if otherwise, nitrogen cannot be dissolved to a uniform depth due to an uneven temperature distribution. Accordingly, the length of the constant-temperature section in the heating chamber is desirably set to keep the temperature unevenness within 10° C.

Before the nitrogen-dissolving treatment, the ferritic stainless steel is desirably treated at a temperature between 700° C. and the nitrogen-dissolving treatment temperature in a hydrogen gas atmosphere at atmospheric pressure, to remove oxides, etc. from the surface. Oxides, etc. on the surface likely act as a barrier to the intrusion of a nitrogen gas, resulting in a low speed and an uneven depth in the nitrogen-dissolving treatment.

With a preheating treatment conducted at a solid solution treatment temperature for 1-3 hours before the nitrogen-dissolving treatment, the austenite phase having a uniform thickness can be formed. Because the preheating treatment time largely depends on grain sizes in the material, it may be set depending on the material.

Heat Treatment

Figure 4A:
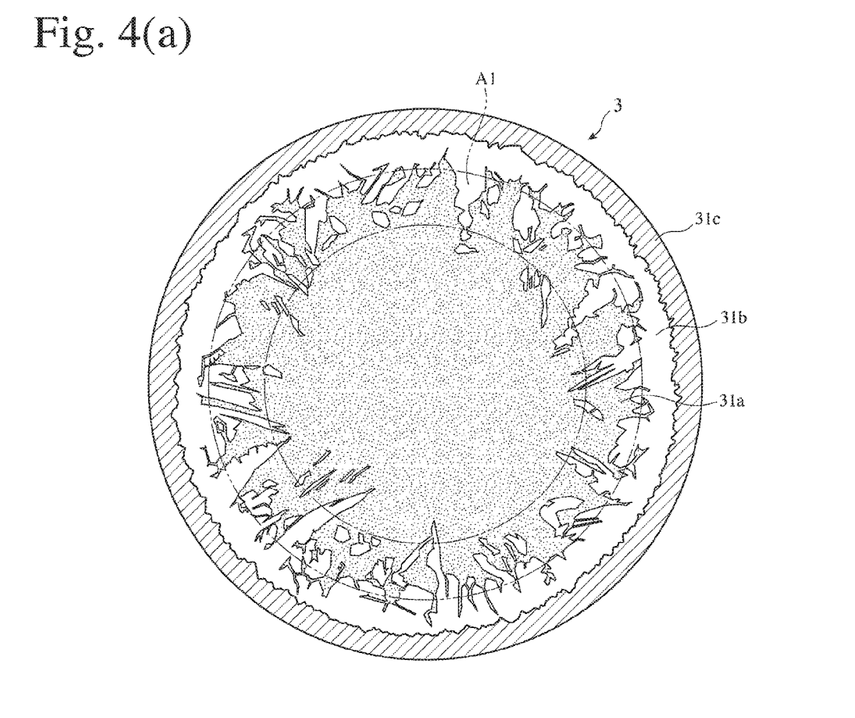
FIG. 4(a) is a schematic view showing a method of laser-heating a boundary region A1 of a ferritic stainless steel center portion and an austenitic stainless steel intermediate portion in the a seal member.
Figure 4B:
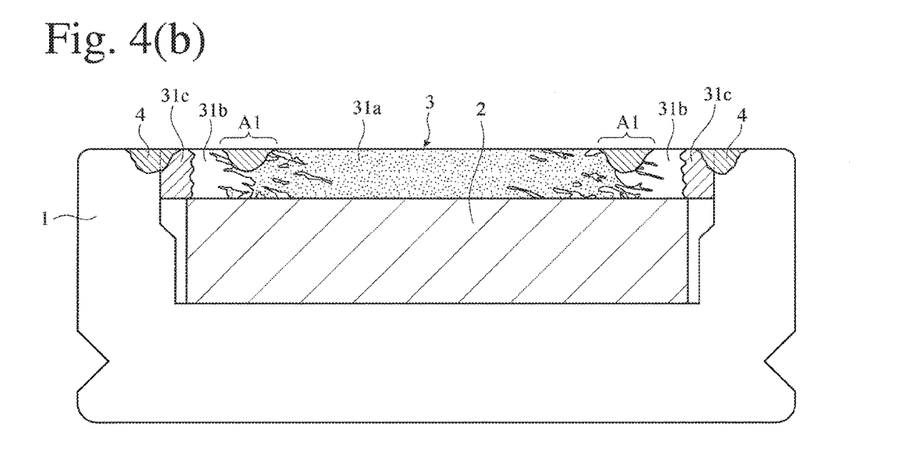
FIG. 4(b) is a schematic cross-sectional view showing a magnet assembly for a magnetic attachment after the boundary region A1 in FIG. 4(a) is heated by laser.

When austenitic stainless steel is formed by a nitrogen-dissolving treatment as described above, the austenitic stainless steel portion $31b$ (intermediate portion $3b$) and the ferritic stainless steel portion $31a$ (center portion $3a$) in the seal member 3 have a jagged boundary as shown in FIG. 2. With such boundary having non-magnetic austenitic stainless steel partially intruding into the center portion $3a$ of the seal member 3, a magnetic circuit constituted by the permanent magnet 2, the cup-shaped yoke 1 and the seal member 3 has reduced efficiency, resulting in low magnetic attraction with differences among products, and thus failing to obtain products having stable performance. To avoid this, as shown in FIGS. 4(a) and 4(b), the boundary region A1 of the austenitic stainless steel portion $31b$ and the ferritic stainless steel portion $31a$ in the seal member 3 may be heated by laser to return the austenitic stainless steel to the ferritic stainless steel. The boundary region A1 is preferably heated only on the surface of the seal member 3, to avoid the magnetic properties of the permanent magnet 2 from being reduced by heat. This can reduce the unevenness of magnetic circuits among the products, providing stable attraction.

(3) Cup-Shaped Yoke

Figure 5:
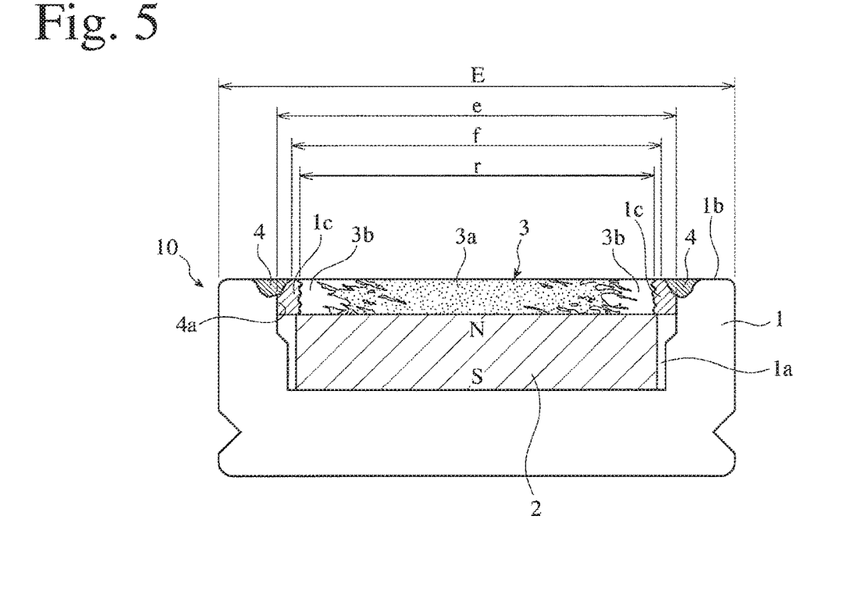
FIG. 5 is a schematic view for explaining the shape of a cup-shaped yoke used in the present invention.

The cup-shaped yoke 1 has a recess $1a$ for receiving a permanent magnet 2. The recess $1a$ has a size suitable for accommodating the permanent magnet 2, and a portion of the recess $1a$ into which the seal member 3 is inserted (near an opening edge, see FIG. 5) preferably has a diameter e set to meet the relation (1):

$$(Br \times S) \times 0.8 \leq Sc \times Bs \leq (Br \times S) \times 1.2,$$

wherein Bs represents the saturation magnetization of the cup-shaped yoke 1, Br represents the residual magnetic flux density of the permanent magnet 2, S represents the area of a cross section of the permanent magnet 2 perpendicular to a magnetization direction, and Sc represents an effective area (magnetic area) of an attracting surface of the cup-shaped yoke 1.

To determine the effective attracting surface area Sc of the cup-shaped yoke 1, increase in a magnetic region by the ferritic stainless steel peripheral portion $3c$ of the seal member 3 should be taken into consideration. Accordingly, the effective attracting surface area Sc of the cup-shaped yoke 1 is a sum of an attracting surface area $Sc_0$ [$=\pi \times (E^2 - e^2)/4$] of the cup-shaped yoke 1 (opening edge portion $1b$ of the cup-shaped yoke 1), and an area $Sc_1$ [$=\pi \times (e^2 - r^2)/4$] of the peripheral portion $3c$ of the seal member 3, wherein E represents an outer diameter of the cup-shaped yoke 1, e represents a diameter of the cup-shaped yoke 1 near its recess opening edge, and r represents an inner diameter of the peripheral portion $3c$ (see FIG. 5). Namely, the effective area Sc is $Sc_0 + Sc_1 = \pi \times (E^2 - r^2)/4$.

Because the welded portion 4 of the cup-shaped yoke 1 and the seal member 3 is made of a ferritized magnetic material like the peripheral portion $3c$, an area $Sc_2$ [$=\pi \times (e^2 - f^2)/4$] of the welded portion 4 in the seal member 3 is larger than the area $Sc_1$ of the peripheral portion $3c$, when the welded portion 4 expands over a radial width of the peripheral portion $3c$ inside the seal member 3, namely, when the inner diameter f of the welded portion 4 is smaller than the inner diameter r of the peripheral portion $3c$. In this case, the effective attracting surface area Sc of the cup-shaped yoke 1 is a sum of the attracting surface area $Sc_0$ of the cup-shaped yoke 1 and the area $Sc_2$ of the welded portion 4 in the seal member 3. Namely, the effective area Sc is $Sc_0 + Sc_2 = \pi \times (E^2 - f^2)/4$.

With the diameter e near the opening edge and the radial length Lc of the peripheral portion of the seal member (or the width of the welded portion 4 in the seal member 3) set to meet the formula (1), sufficient attraction can be obtained with low magnetic flux density leak. Accordingly, the diameter e of a portion into which the seal member 3 is inserted is desirably determined, taking into consideration the radial length Lc of the peripheral portion (magnetic region) (or the width of the welded portion 4 in the seal member 3). With such an expanded recess $1a$ near its opening edge, the intermediate portion $3b$ (non-magnetic austenitic stainless steel portion) of the seal member 3 can be arranged at an optimum position to the permanent magnet 2.

The cup-shaped yoke 1 is preferably made of corrosion-resistant, soft-magnetic ferritic stainless steel (SUS447J1, SUSXM27, SUS444, etc.). The cup-shaped yoke 1 has a Cr content of preferably 17-32% by mass, more preferably 24-32% by mass.

(4) Welded Portion

Figure 6:
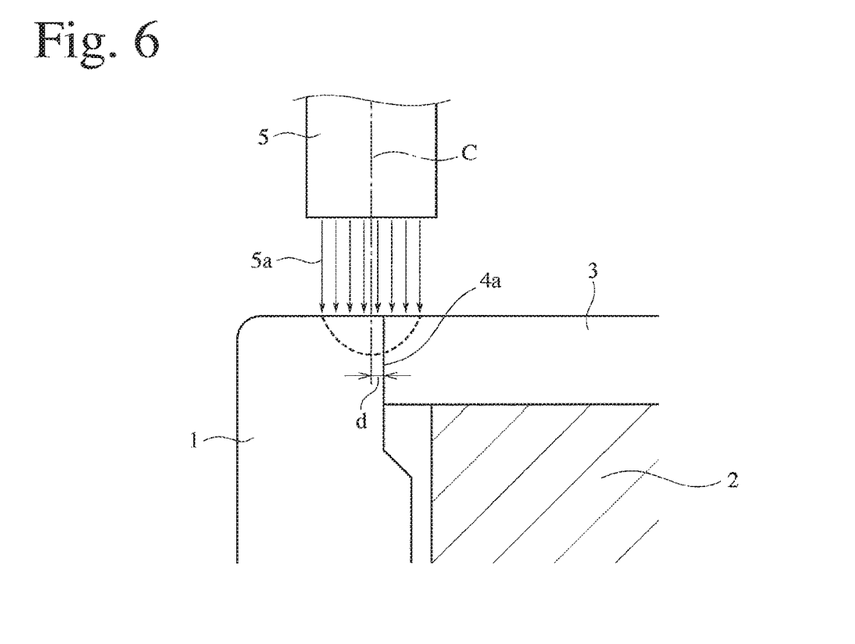
FIG. 6 is a schematic cross-sectional view showing the welding of the abutted seal member and cup-shaped yoke by a laser-radiating means.

As shown in FIG. 1(b), the abutment-welded portion 4 of the seal member 3 and the cup-shaped yoke 1 preferably has a center deviated from the abutment boundary $4a$ of the seal member 3 and the cup-shaped yoke 1 toward the cup-shaped yoke 1. Thus, as shown in FIG. 6, the abutment portion $4a$ is welded by laser beams $5a$ supplied from a laser-radiating means 5, with an optical center axis C of the laser beams $5a$ deviated from the abutment boundary $4a$ of the seal member 3 and the cup-shaped yoke 1 by a distance d toward the cup-shaped yoke 1. The distance d is preferably 3-40%, more preferably 5-30%, of the diameter of laser beams $5a$.

A metal portion irradiated with laser beams $5a$ is melted by heating to a high temperature, so that the cup-shaped yoke 1 is welded to the seal member 3. The peripheral portion 3c of the seal member 3 is ferritized by denitriding, so that it becomes magnetic. However, the intermediate portion 3b and the peripheral portion 3c have a jagged boundary, in which nitrogen-containing austenitic stainless steel (intermediate portion 3b) may partially intrude into the peripheral portion 3c near the periphery 3d. In such a case, a trace amount of dissolved nitrogen may be released, likely causing cracking and voids. Accordingly, the optical axis of laser beams is preferably deviated toward the cup-shaped yoke.

With welding conducted at a position deviated from the abutment boundary 4a toward the cup-shaped yoke 1, and with a heating range of the ferritic stainless steel peripheral portion 3c made as small as possible, a heating range of the intermediate portion 3b of nitrogen-dissolved austenitic stainless steel is made as small as possible to suppress the discharge of nitrogen by heating, so that defects due to the discharge of nitrogen can be suppressed, resulting in a magnet assembly having high magnetic attraction as well as excellent corrosion resistance and durability.

To remove unevenness, the welded portion 4 is preferably machined flat to a predetermined depth. The machining is preferably the polishing of the cup-shaped yoke 1, the seal member 3 and the welded portion 4 to such a depth as to avoid decrease in welding strength.

(5) Permanent Magnet

The permanent magnet 2 is preferably a neodymium magnet having a larger residual magnetic flux density Br than those of other permanent magnets for larger attraction. Because the magnetic circuit should be saturated, the residual magnetic flux density Br of the neodymium magnet is preferably 1.3 T or more, more preferably 1.35 T or more. The permanent magnet 2 is magnetized after assembled in the magnet assembly.

The present invention will be explained in more detail by Examples below, without intention of restriction.

Example 1

Figure 7:
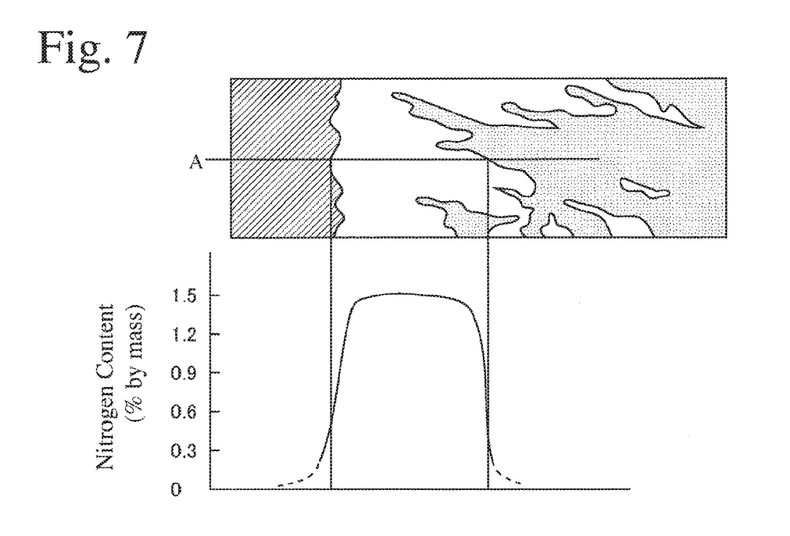
FIG. 7 is a graph showing a nitrogen content distribution in the seal member in a radial direction (along the line A).

After a round rod of 2.7 mm in diameter and 60 mm in length made of ferritic stainless steel (SUSXM27) having a composition comprising 26% by mass of Cr, and 1% by mass of Mo, the balance being Fe (containing 0.08% by mass of Ni as an impurity), was charged into a cooling chamber in a furnace kept at 1200° C., the atmosphere in the furnace was changed to a nitrogen gas atmosphere at atmospheric pressure. The round rod was moved to a heating chamber in the furnace, and kept there for 3 hours. With the nitrogen gas pressure lowered to 0.1 MPa, the round rod was further kept in the heating chamber for 10 minutes. Thereafter, the round rod was returned to the cooling chamber for rapid cooling, thereby conducting a nitrogen-dissolving treatment to the ferritic stainless steel round rod. The measurement by EPMA (JXA-8900 available from JEOL Ltd.) of a transverse cross section of the round rod taken out of the furnace revealed that a concentric outer layer (peripheral portion) of ferritic stainless steel was formed to the depth of about 100 μm from the peripheral surface, that a concentric intermediate layer of austenitic stainless steel was formed to the width of about 200 μm inside the concentric outer layer, and that inside the concentric intermediate layer was a center portion of the original ferritic stainless steel. The peripheral portion, the intermediate portion and the center portion had nitrogen contents of less than 0.2% by mass, 1.5% by mass and less than 0.2% by mass, respectively. A nitrogen content distribution in the round rod in a radial direction (along the line A) from the center is schematically shown in FIG. 7. This round rod was cut to a disc-shaped seal member having an axial thickness of 0.25 mm.

Produced by ferritic stainless steel having the same composition as for the seal member was a cylindrical cup-shaped yoke of 3.5 mm in diameter and 1.35 mm in height, and a recess having a hole portion of 2.6 mm in diameter into which a neodymium magnet was placed, and an opening edge portion of 2.7 mm in diameter and 0.75 mm in depth into which the seal member was inserted. A neodymium magnet of 2.6 mm in diameter and 0.5 mm in thickness was placed in the recess of the cup-shaped yoke, and an opening of the recess was closed by the seal member as a lid.

Figure 8A:
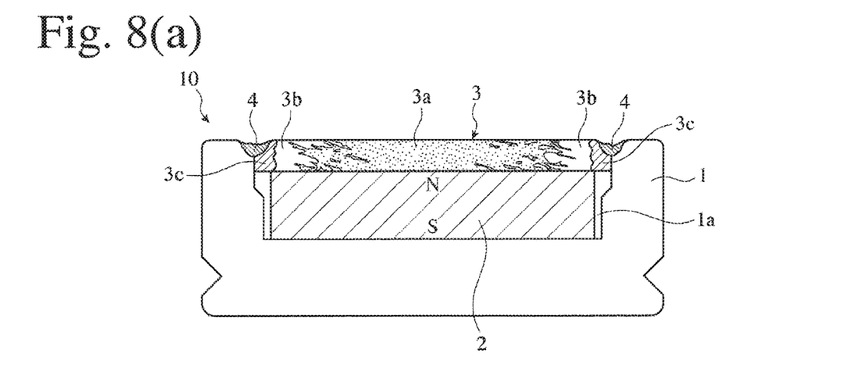
FIG. 8(a) is a schematic cross-sectional view showing the magnet assembly for a magnetic attachment in Example 1.
Figure 8B:
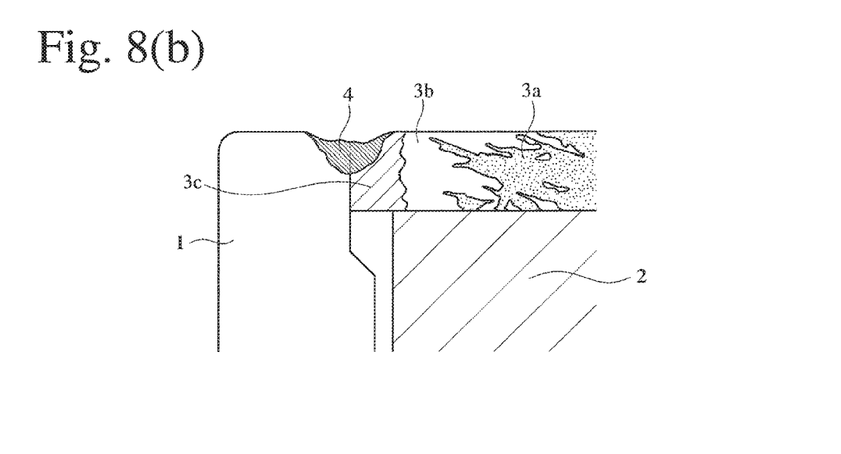
FIG. 8(b) is a schematic cross-sectional view enlargedly showing the welded portion in FIG. 8(a).

As shown in FIGS. 8(a) and 8(b), the abutment portion 4a of the cup-shaped yoke 1 and the seal member 3 was irradiated with laser beams 5a (beam diameter: 200 μm) supplied from a laser-radiating means 5, such that an optical center axis of laser beams 5a was aligned with the seal member 3. As a result, the abutment boundary 4a was sealed by welding over the entire circumferential length.

The welded surface was polished flat by 0.05 mm, to produce a magnet assembly of 3.5 mm in diameter and 1.3 mm in height. This magnet assembly had magnetic attraction of 5.1-5.2 N (measured 5 times). On the other hand, a conventional magnet assembly having the same diameter and height as in Example 1 with a disc-shaped seal member consisting of a disc yoke and a seal ring (300 μm wide) described in JP 5-95965 A had magnetic attraction of 5.0-5.2 N (measured 5 times).

Example 2

A magnet assembly was produced in the same manner as in Example 1, except that when the abutment portion of a cup-shaped yoke and a seal member was welded, an optical center axis C of laser beams 5a was deviated outward from the abutment boundary by a distance d of 20 μm toward the cup-shaped yoke, as shown in FIG. 6. There was no dent or crack in the welded portion. The measured magnetic attraction of this magnet assembly was 5.1-5.2 N (measured 5 times).

Example 3

A magnet assembly was produced in the same manner as in Example 1, except that when the abutment portion of a cup-shaped yoke and a seal member was welded, an optical center axis of laser beams 5a was deviated outward from the abutment boundary by a distance d of 40 μm toward the cup-shaped yoke. None of welded portions in 10 samples produced had a dent or crack. The measured magnetic attraction of this magnet assembly was 5.1-5.2 N (measured 5 times).

Example 4

A magnet assembly was produced in the same manner as in Example 1, except that when the abutment portion of a cup-shaped yoke and a seal member was laser-welded, an optical center axis of laser beams 5a was deviated outward from the abutment boundary by a distance d of 40 μm toward the cup-shaped yoke, and that a circular portion having a radius of 1.05 mm from a center of the seal member 3 was irradiated along its entire length with laser beams 5a (beam diameter 200 μm φ) whose optical center axis C was aligned with the circular portion, thereby heating a boundary region A1, as shown in FIG. 4(a). A boundary portion (0.2 mm wide and about 0.15 mm deep) of the center portion and the intermediate portion was ferritized by this heating (before polishing). This magnet assembly had magnetic attraction of 5.2-5.4 N (measured 5 times). Improvement in the magnetic attraction appears to be due to the heating of the boundary region of the austenitic stainless steel portion and the ferritic stainless steel portion in the seal member, resulting in reduced unevenness in the boundary, and thus a proper magnetic path on the attracting surface.

What is claimed is:

1. A magnet assembly for a dental magnetic attachment comprising: a cup-shaped yoke of substantially Ni-free ferritic stainless steel, a permanent magnet received in a recess of said cup-shaped yoke, a seal member sealing an opening of said cup-shaped yoke, and an abutment-welded portion of said seal member and said cup-shaped yoke; said seal member integrally comprising:
- a center portion of substantially Ni-free ferritic stainless steel;
- an intermediate portion outside said center portion, which is made of substantially Ni-free austenitic stainless steel having a nitrogen content of 0.5-2.0% by mass; and
- a peripheral portion outside said intermediate portion, which is made of substantially Ni-free ferritic stainless steel having a nitrogen content of 1.3% or less by mass, wherein the nitrogen content in said peripheral portion is smaller than that in said intermediate portion,
- wherein said cup-shaped yoke and said seal member have a Ni content of 0.2% or less by mass, and
- wherein the abutment-welded portion welds said peripheral portion of said seal member to said cup-shaped yoke.

2. The magnet assembly for a dental magnetic attachment according to claim 1, wherein a center of said welded portion is deviated from an abutment boundary of said seal member and said cup-shaped yoke toward said cup-shaped yoke.

3. The magnet assembly for a dental magnetic attachment according to claim 1, wherein said cup-shaped yoke and said seal member have a Cr content of 17-32% by mass.

4. The magnet assembly for a dental magnetic attachment according to claim 1, wherein the average radial length of said peripheral portion is 20-80% of the radial length of said welded portion.

5. The magnet assembly for a dental magnetic attachment according to claim 1, wherein the average radial length of said peripheral portion is 50-400 μm.

6. The magnet assembly for a dental magnetic attachment according to claim 1, wherein the average radial length of said intermediate portion is 50-400 μm.

7. The magnet assembly for a dental magnetic attachment according to claim 1, wherein the average radial length of said intermediate portion is larger than the average radial length of said peripheral portion.

8. The magnet assembly for a dental magnetic attachment according to claim 1, wherein part of the austenitic stainless steel of said intermediate portion is transformed to a ferrite phase or a mixed phase of ferrite and Cr nitride by heating, in a boundary of the austenitic stainless steel of said intermediate portion and the ferritic stainless steel of said center portion.

9. The magnet assembly for a dental magnetic attachment according to claim 1, wherein said seal member is obtained by cutting a round rod to a disc, the round rod integrally having a core portion of ferritic stainless steel, an intermediate portion of austenitic stainless steel, and a surface layer portion of ferritic stainless steel.

10. The magnet assembly for a dental magnetic attachment according to claim 1, wherein the nitrogen content in said intermediate portion is 1-2.0% by mass.

11. The magnet assembly for a dental magnetic attachment according to claim 1, wherein the nitrogen content in said intermediate portion is 1.5-2.0% by mass.

12. The magnet assembly for a dental magnetic attachment according to claim 1, wherein the nitrogen content in said intermediate portion is greater than 1% by mass and less than or equal to 2.0% by mass.

13. The magnet assembly for a dental magnetic attachment according to claim 2, wherein the center of the welded portion is deviated by 20 μm from the abutment boundary of said seal member and said cup-shaped yoke toward said cup-shaped yoke.

14. A method for producing a magnet assembly for a dental magnetic attachment comprising: a cup-shaped yoke of substantially Ni-free ferritic stainless steel, a permanent magnet received in a recess of said cup-shaped yoke, a seal member sealing an opening of said cup-shaped yoke, and an abutment-welded portion of said seal member and said cup-shaped yoke; said seal member integrally comprising:
- a center portion of substantially Ni-free ferritic stainless steel;
- an intermediate portion outside said center portion, which is made of substantially Ni-free austenitic stainless steel having a nitrogen content of 0.5-2.0% by mass; and
- a peripheral portion outside said intermediate portion, which is made of substantially Ni-free ferritic stainless steel having a nitrogen content of 1.3% or less by mass, wherein the nitrogen content in said peripheral portion is smaller than that in said intermediate portion,
- wherein said cup-shaped yoke and said seal member have a Ni content of 0.2% or less by mass, and
- wherein the abutment-welded portion welds said peripheral portion of said seal member to said cup-shaped yoke, comprising the steps of placing the permanent magnet in the recess of the cup-shaped yoke of substantially Ni-free ferritic stainless steel, inserting the disc-shaped seal member into an opening of the recess, and welding an abutment portion of the cup-shaped yoke and the seal member,
- wherein the seal member is obtained by subjecting a round rod of substantially Ni-free ferritic stainless steel to a nitrogen-dissolving treatment to austenize a surface layer of the round rod to a predetermined depth, denitriding a surface portion of the austenized portion for ferritization, and then transversely cutting the round rod to a disc shape.

* * * * *